United States Patent
Wilkerson et al.

(10) Patent No.: US 11,491,302 B2
(45) Date of Patent: Nov. 8, 2022

(54) SYSTEM AND METHODS FOR TRIGGERING SOUNDS TO MASK NOISE FROM RESPIRATORY SYSTEMS AND THEIR COMPONENTS

(71) Applicants: ResMed Corp., San Diego, CA (US);
ResMed inc., San Diego, CA (US);
ResMed Sensor Technologies Limited, Dublin (IE)

(72) Inventors: Shawna Wilkerson, Encinitas, CA (US); Gregory Robert Peake, Sydney (AU); Redmond Shouldice, Dublin (IE); Ryan Mathew Hernandez, Encinitas, CA (US)

(73) Assignee: ResMed Sensor Technologies Limited, Dublin (IE)

( * ) Notice: Subject to any disclaimer, the term of this patent is extended or adjusted under 35 U.S.C. 154(b) by 0 days.

(21) Appl. No.: 17/441,627

(22) PCT Filed: Jun. 26, 2020

(86) PCT No.: PCT/US2020/039992
§ 371 (c)(1),
(2) Date: Sep. 21, 2021

(87) PCT Pub. No.: WO2020/264427
PCT Pub. Date: Dec. 30, 2020

(65) Prior Publication Data
US 2022/0126056 A1    Apr. 28, 2022

Related U.S. Application Data

(60) Provisional application No. 62/890,918, filed on Aug. 23, 2019, provisional application No. 62/868,465, filed on Jun. 28, 2019.

(51) Int. Cl.
*A61M 21/02* (2006.01)
*G10K 11/175* (2006.01)
(Continued)

(52) U.S. Cl.
CPC ............ *A61M 21/02* (2013.01); *A61M 16/06* (2013.01); *G10K 11/1752* (2020.05);
(Continued)

(58) Field of Classification Search
CPC .................. A61M 21/02; A61M 16/06; A61M 2021/0027; A61M 2205/15;
(Continued)

(56) References Cited

U.S. PATENT DOCUMENTS 5,844,996 A * 12/1998 Enzmann .................. A61F 5/56
                                                      704/E21.014
7,448,382 B1 * 11/2008 Alexander ........ A61M 16/0063
                                                      128/204.23
(Continued)

FOREIGN PATENT DOCUMENTS

WO    2018039433 A1    3/2018
WO    2019122412 A1    6/2019

OTHER PUBLICATIONS

International Search Report in International Patent Application No. PCT/US2020/039992 dated Nov. 18. 2020 (7 pp.).
(Continued)

*Primary Examiner* — Sunita Reddy
(74) *Attorney, Agent, or Firm* — Nixon Peabody LLP (57) ABSTRACT

A system includes a respiratory device, a mask, a microphone, a speaker, and a control system. The respiratory device is configured to supply pressurized air. The mask is coupled to the respiratory device and configured to engage a user during a sleep session to aid in directing the supplied pressurized air to the user. The microphone is configured to
(Continued)

generate audio data. The speaker is configured to emit sound. The control system is configured to analyze the audio data to determine if noise associated with air leaking from the mask is occurring. Responsive to (i) the analysis resulting in a determination that noise associated with air leaking from the mask is occurring, (ii) the respiratory device determining that air is leaking from the mask, or (iii) both, the speaker is caused to emit the sound to aid in masking the noise associated with the air leaking from the mask.

28 Claims, 6 Drawing Sheets

(51) Int. Cl.
| | | |
|---|---|---|
| *H04R 1/40* | (2006.01) | |
| *H04R 3/00* | (2006.01) | |
| *H04R 1/02* | (2006.01) | |
| *A61M 16/06* | (2006.01) | |
| *A61M 21/00* | (2006.01) | |

(52) U.S. Cl.
CPC ............. *H04R 1/028* (2013.01); *H04R 1/406* (2013.01); *H04R 3/005* (2013.01); *A61M 2021/0027* (2013.01); *A61M 2205/15* (2013.01); *A61M 2205/3306* (2013.01); *A61M 2205/3331* (2013.01); *A61M 2205/3375* (2013.01); *A61M 2230/63* (2013.01); *H04R 2430/01* (2013.01)

(58) Field of Classification Search
CPC .. A61M 2205/3306; A61M 2205/3331; A61M 2205/3375; A61M 2230/63; G10K 11/1752; H04R 1/028; H04R 1/406; H04R 3/005; H04R 2430/01
USPC ..................................................... 600/26–28
See application file for complete search history.

(56) References Cited

U.S. PATENT DOCUMENTS

| | | | |
|---|---|---|---|
| 2005/0226435 A1* | 10/2005 | Steer ................ | G10K 11/17875 |
| | | | 381/71.7 |
| 2008/0078248 A1 | 4/2008 | Farbarik | |
| 2009/0147965 A1* | 6/2009 | Kuo ...................... | A47C 21/003 |
| | | | 379/420.01 |
| 2010/0258123 A1 | 10/2010 | Somaiya et al. | |
| 2013/0070934 A1 | 3/2013 | Kuo | |
| 2015/0190609 A1 | 7/2015 | Miwa | |
| 2015/0320960 A1* | 11/2015 | Barlow ............. | A61M 16/0683 |
| | | | 128/205.25 |
| 2015/0352308 A1* | 12/2015 | Cullen ............. | A61M 16/0683 |
| | | | 128/205.25 |
| 2016/0206836 A1* | 7/2016 | Kuo ................ | A61M 16/0003 |
| 2016/0270718 A1 | 9/2016 | Heneghan et al. | |
| 2017/0246408 A1 | 8/2017 | Kwok et al. | |

OTHER PUBLICATIONS

Written Opinion in International Patent Application No. PCT/US2020/03992 dated Nov. 18, 2020.

* cited by examiner

SYSTEM AND METHODS FOR TRIGGERING SOUNDS TO MASK NOISE FROM RESPIRATORY SYSTEMS AND THEIR COMPONENTS

CROSS-REFERENCE TO RELATED APPLICATIONS

This application is a U.S. National Stage of International Application No. PCT/US2020/039992, filed Jun. 26, 2020, which claims the benefit of and priority to U.S. Provisional Application No. 62/868,465, filed Jun. 28, 2019, and U.S. Provisional Application No. 62/890,918, filed Aug. 23, 2019, each of which is hereby incorporated by reference herein in its entirety.

TECHNICAL FIELD

The present disclosure relates to treatment of respiratory-related disorders and more specifically to systems and methods for detecting and mitigating the effect of noise caused by respiratory devices and its components.

BACKGROUND

Various systems exist for aiding users experiencing sleep apnea and related respiratory disorders. A range of respiratory disorders exist that can impact users. Certain disorders are characterized by particular events (e.g., apneas, hypopneas, hyperpneas, or any combination thereof). Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and Chest wall disorders. A person with respiratory disorder can have trouble sleeping, but systems designed to mitigate physical symptoms of the respiratory disorder do not address issues outside of the symptoms of the disorder itself that can keep the person from sleeping well.

Thus, a need exists for alternative systems and methods for addressing sleep disturbances related to treatments for respiratory disorders. The present disclosure is directed to solving these problems and addressing other needs.

SUMMARY

According to some implementations of the present disclosure, a method includes receiving first audio data from a first microphone. The first audio data is analyzed to determine if noise associated with air leaking from a mask is occurring. The mask is coupled to a respiratory device supplying pressurized air, and the mask is configured to engage a user during a sleep session to aid in directing the supplied pressurized air to an airway of the user. A speaker is caused to emit sound based at least in part on a result of the analysis of the first audio data.

According to some implementations of the present disclosure, a method includes receiving audio data from a microphone. The audio data is analyzed to determine (i) if background noise associated with one or more background devices is present and (ii) if operational noise associated with operation of a respiratory device, a mask, a tube, or any combination thereof is occurring. The mask is coupled to the respiratory device via the tube. The mask is configured to engage a user during a sleep session to aid in directing supplied pressurized air to an airway of the user. Responsive to the analysis of the audio data resulting in a determination that (i) background noise is present and (ii) operational noise is occurring, a speaker is caused to emit sound to aid in masking the operational noise, the sound emitted by the speaker having a plurality of characteristics, at least a portion of the plurality of characteristics being based at least in part on one or more characteristics of the background noise.

According to some implementations of the present disclosure, a method includes causing a source of air to deliver air into a humidification tank to cause air bubbles to form and float up through water stored in the humidification tank, thereby generating a bubbling sound. The humidification tank is coupled to a respiratory device and configured to store the water. A mask is coupled to the respiratory device via a tube and being configured to engage a user during a sleep session to aid in directing supplied pressurized air to an airway of the user According to some implementations of the present disclosure, a system for masking noises generated during use of a respiratory device is provided. The system includes a respiratory device, a mask, a microphone, a speaker, a memory, and a control system. The respiratory device is configured to supply pressurized air. The mask is coupled to the respiratory device and is configured to engage a user during a sleep session to aid in directing the supplied pressurized air to an airway of the user. The microphone is configured to generate audio data. The speaker is configured to emit sound. The memory is configured to store machine-readable instructions. The control system includes one or more processors configured to execute the machine-readable instructions to: analyze the audio data to determine if noise associated with air leaking from the mask is occurring; and responsive to (i) the analysis resulting in a determination that noise associated with air leaking from the mask is occurring, (ii) the respiratory device determining that air is leaking from the mask, or (iii) both (i) and (ii), cause the speaker to emit the sound to aid in masking the noise associated with the air leaking from the mask.

According to some implementations of the present disclosure, a system for masking noises generated during use of a respiratory device is provided. The system includes a respiratory device, a mask, a first microphone, a second microphone, a speaker, a memory, and a control system. The respiratory device is configured to supply pressurized air. The mask is coupled to the respiratory device and is configured to engage a user during a sleep session to aid in directing the supplied pressurized air to an airway of the user. The first microphone is configured to generate first audio data. The second microphone is configured to generate second audio data. The speaker is configured to emit sound. The memory is configured to store machine-readable instructions. The control system includes one or more processors configured to execute the machine-readable instructions to: analyze the first audio data to determine if noise associated with air leaking from the mask is occurring; and responsive to (i) the analysis of the first audio data resulting in a determination that noise associated with air leaking from the mask is occurring, (ii) the respiratory device determining that air is leaking from the mask, or (iii) both (i) and (ii), analyze the second audio data to determine if a bed partner of the user is presently disturbed; and responsive to the analysis of the second audio data resulting in a determination that the bed partner is presently disturbed, cause the speaker to emit the sound.

According to some implementations of the present disclosure, a system including a respiratory device, a mask, a speaker, a memory, and a control system is provided. The respiratory device is configured to supply pressurized air. The mask is coupled to the respiratory device and is configured to engage a user during a sleep session to aid in directing the supplied pressurized air to an airway of the user. The speaker is configured to emit sound. The memory is configured to store machine-readable instructions. The control system includes one or more processors configured to execute the machine-readable instructions to, responsive to the respiratory device determining that air is leaking from the mask, cause the speaker to emit the sound to aid in masking noise associated with the air leaking from the mask.

According to some implementations of the present disclosure, a system including a respiratory device, a mask, a microphone, a speaker, a memory, and a control system is provided. The respiratory device is configured to supply pressurized air. The mask is coupled to the respiratory device and is configured to engage a user during a sleep session to aid in directing the supplied pressurized air to an airway of the user. The microphone is configured to generate audio data. The speaker is configured to emit sound. The memory is configured to store machine-readable instructions. The control system includes one or more processors configured to execute the machine-readable instructions to: analyze the audio data to determine if noise associated with air leaking from the mask is occurring; and responsive to the analysis resulting in a determination that noise associated with air leaking from the mask is occurring, cause the speaker to start emitting the sound to aid in masking the noise associated with the air leaking from the mask.

According to some implementations of the present disclosure, a system for masking noises generated during use of a respiratory device includes a respiratory device, a mask, a microphone, a speaker, a memory, and a control system. The respiratory device is configured to supply pressurized air. The mask is coupled to the respiratory device via a tube and is configured to engage a user during a sleep session to aid in directing the supplied pressurized air to an airway of the user. The microphone is configured to generate audio data. The memory stores machine-readable instructions. The control system includes one or more processors configured to execute the machine-readable instructions to analyze the audio data. The analysis of the audio data determines (i) if background noise associated with one or more background devices is present and (ii) if operational noise associated with operation of the respiratory device, the mask, the tube, or any combination thereof is occurring. Responsive to the analysis resulting in a determination that (i) background noise is present and (ii) operational noise is occurring, the control system causes the speaker to emit sound to aid in masking the operational noise. The sound emitted by the speaker has a plurality of characteristics. At least a portion of the plurality of characteristics is based at least in part on one or more characteristics of the background noise.

According to some implementations of the present disclosure, a system for masking noises generated during use of a respiratory device includes a respiratory device, a humidification tank, a mask, a memory, and a control system. The respiratory device is configured to supply pressurized air. The humidification tank is coupled to the respiratory device and configured to store water therein. The mask is coupled to the respiratory device via a tube and is configured to engage a user during a sleep session to aid in directing the supplied pressurized air to an airway of the user. The memory stores machine-readable instructions. The control system includes one or more processors configured to execute the machine-readable instructions to cause a source of air to deliver air into the humidification tank to cause air bubbles to form and float up through the water stored in the humidification tank, thereby generating a bubbling sound.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

Figure 1:
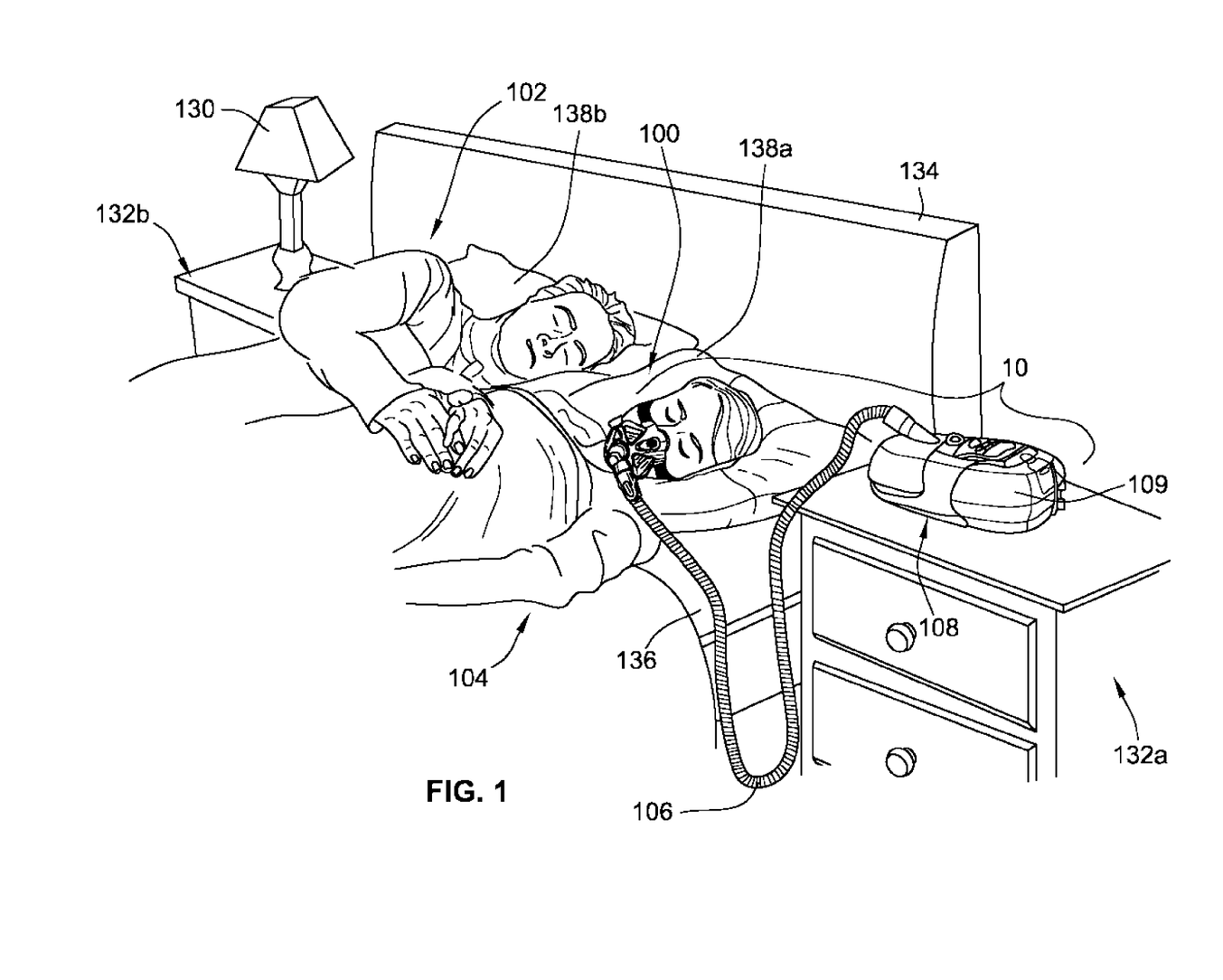
FIG. 1 illustrates a bedroom with a user, a bed partner, and a respiratory system, according to some implementations of the present disclosure.

FIG. 1 illustrates an environment for mitigating effects of noise from a respiratory device, system, and/or any of its components (e.g., mask, motor, water tank, pump, etc.), according to some implementations of the present disclosure. The environment is a bedroom setting that includes a respirator user 104 and a bed partner 102 lying on a bed with a mattress 136, pillows 138a and 138b, and headboard 134. Next to the bed are two nightstands 132a and 132b, and a lamp 130 on the nightstand 132b. The respirator user 104 is wearing a user interface (e.g., a mask 100) connected via an air circuit or a conduit (e.g., a tube or a tubing 106) to a respirator or respiratory device 108. The mask 100, the air circuit or tubing 106, and the respirator 108 can be collectively referred to as a respiratory system 10. In some implementations, the respiratory system 10 includes a humidification tank 109 that can be used to store water and generate humidity in the supplied air to the respirator user 104.

The respiratory system 10 can be used, for example, as a positive airway pressure (PAP) system, a continuous positive airway pressure (CPAP) system, an automatic positive airway pressure system (APAP), a bi-level or variable positive airway pressure system (BPAP or VPAP), a ventilator, or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

The respirator user 104 may suffer from obstructive sleep apnea and relies on the mask 100 to deliver pressurized air from the respiratory device 108 via the tubing 106. The respiratory device 108 can be a CPAP machine used to increase air pressure in the throat of the respirator user 104 to prevent the airway from closing and/or narrowing during sleep. For someone with sleep apnea, her airway can narrow or collapse during sleep, reducing oxygen intake, and forcing her to wake up and/or otherwise disrupt her sleep. The CPAP machine prevents the airway from narrowing or collapsing thus minimizing the occurrences where she wakes up or is otherwise disturbed due to reduction in oxygen intake.

The respiratory device 108 strives to maintain a medically prescribed air pressure during sleep, but in some cases, the mask 100 may move or become repositioned while the respirator user 104 is asleep. The movement of the mask 100 can cause and/or allow air from the respiratory device 108 to leak at an interface between the mask 100 and face of the respirator user 104. For example, the respirator user 104 may be suggested to sleep on her back while sleeping with the mask 100 on, but during the course of a night's rest, the respirator user 104 unconsciously changes position such that her cheek becomes flush against the pillow 138a. In this new position, the mask 100 can move from a snug position that prevented air leakage to a new position that allows air from the respiratory device 108 to leak. Pressurized air leaking from the mask 100 can make audible noise that disturbs the respirator user 104 and/or the bed partner 102, thus interfering with and/or negatively influencing both parties' sleeping session.

Other sources for air leaks at the interface between the mask 100 and face of the respirator user 104 are possible. For example, over time, the mask 100 or a portion thereof may become worn such that the seal at the interface is not as complete as when the mask 100 was new. For another example, strap segments 205a, 205b, and 205c (FIG. 2) of the mask 100 can become loosened over time resulting in a poor seal that may cause air leaks.

Figure 2:
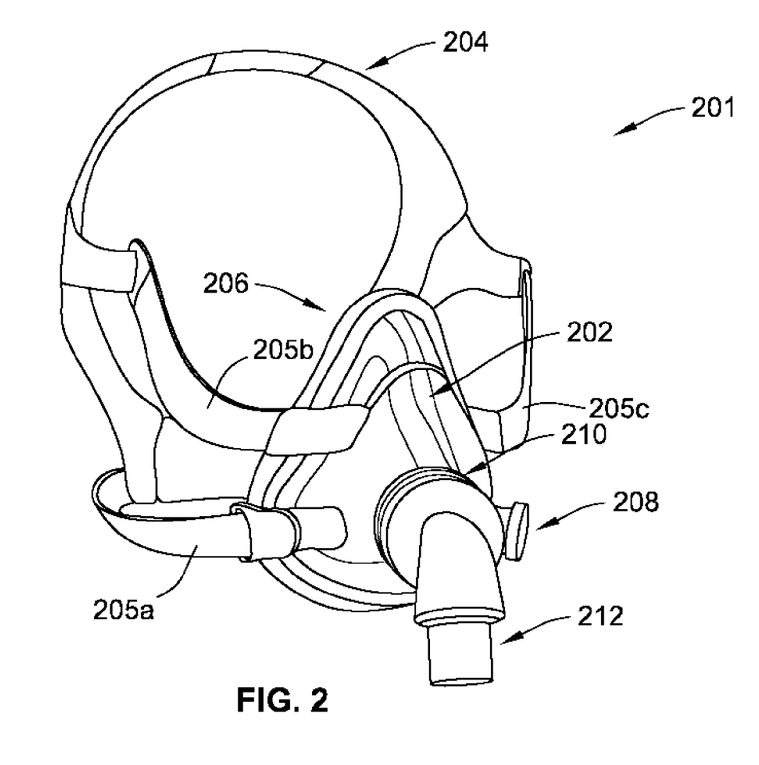
FIG. 2 is a perspective view of a mask or mask assembly of the respiratory system of FIG. 1, according to some implementations of the present disclosure.

Referring to FIG. 2, a mask 201 for use with a respiratory device (e.g., the respiratory device 108) is shown according to some implementations of the present disclosure. The mask 201, is the same as, or similar to, the mask 100 of FIG. 1. The mask 201 includes a plenum chamber 202, a positioning or stabilizing structure 204 with strap segments 205a, 205b, and 205c, a cushion 206, an electronics interface 208, a connecting section 210, and a connection port or coupling mechanism 212. The positioning or stabilizing structure 204 allows a respirator user, e.g., the respirator user 104, to affix the plenum chamber 202 snugly to her face. The cushion 206 is provided between the face of the respirator user 104 and the plenum chamber 202 to improve comfort to the wearer and also to act as a seal or a conforming membrane for preventing pressurized air from leaking out of the plenum chamber 202 at the interface between the face of the respirator user 104 and the plenum chamber 202. The cushion 206 can be made from silicone.

The connecting section 210 allows attachment of the connection port 212 to the plenum chamber 202. The connection port 212 mates with a tubing, e.g., the tubing 106, for receiving pressurized air from the respiratory device 108. The connecting section 210 can provide a swivel such that the connection port 212 can be rotated to a desired position. The connection section 210 can also provide controlled vents to allow carbon dioxide and other gases exhaled by the respirator user 104 to escape the plenum chamber 202. The controlled vents can allow continuous vent flow from an interior of the plenum chamber 202 to ambient whilst the pressure within the plenum chamber 202 is positive with respect to the ambient. The controlled vents at the connection section 210 are structured such that the vent flowrate has a magnitude sufficient to reduce rebreathing of exhaled carbon dioxide by the respirator user 104, while maintaining the therapeutic pressure in the plenum chamber 202.

In some implementations, the mask 201 includes one or more supplementary ports that allow access to volume within the plenum chamber 202. The supplementary port(s) can allow a clinician or physician to probe or access property of gases within the plenum chamber 202. For example, the supplemental port can aid in determining pressure within the plenum chamber 202.

The electronics interface 208 provides connection to electronic sensors and other devices that can be embedded in the mask 201. Although the strap segments 205a, 205b, and 205c are provided to allow a snug fit of the mask 201 to the respirator user 104, while sleeping, the respirator user 104 moving or changing sleeping position can disturb this snug fit, allowing pressurized air to leak from the mask 201. The pressurized air can cause noise, which can disturb those sleeping in the vicinity (e.g., the bed partner 102 shown in FIG. 1).

Figure 3:
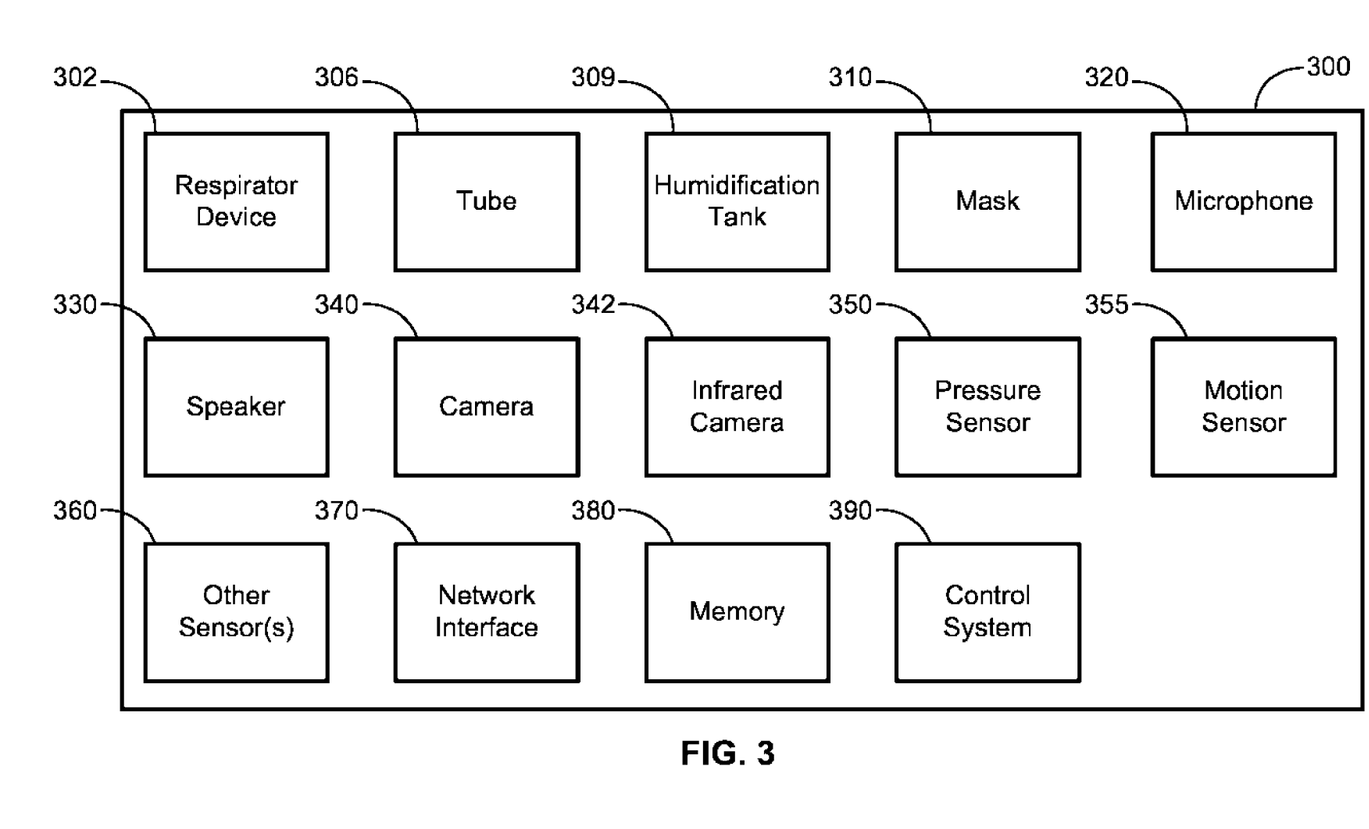
FIG. 3 is a block diagram of a system for mitigating noise generated by a respiratory system and/or its components, according to some implementations of the present disclosure.

Referring to FIG. 3, a block diagram of a system 300 for mitigating effects of noise from a respiratory device 302 (or from a mask 310 attached to the respiratory device 302 via tube 306) is shown according to some implementations of the present disclosure. To simplify discussion, the singular form will be used for all components identified in FIG. 3 when appropriate, but the use of the singular does not limit the discussion to only one of each such component.

The respiratory device 302, the mask 310, and the tube 306, are the same as, or similar to, the respiratory device 108 (e.g., a CPAP machine), the mask 100, and the tube 106 shown in FIG. 1 and described herein. The respiratory device 302 can include a humidification tank 309, which is the same as, or similar to, the humidification tank 109 (FIG. 1). The mask 310 is the same as, or similar to the mask 201 and/or the mask 100. The mask 310 can be worn by or donned upon the respirator user 104 (FIG. 1). The respiratory device 302 can be configured to generate a flow of air for delivery to the airways of the respirator user 104. The respiratory device 302 can deliver air flow in a range of −20 L/min to 150 L/min while maintaining a positive pressure of at least 6 cm $H_2O$, or at least 10 cm $H_2O$, or at least 20 cm H₂O. The respiratory device 302 can include an external housing with one or more panels and a handle.

The respiratory device 302 can also include an inlet air filter, an inlet muffler, a pressure generator for supplying air at positive pressure, an outlet muffler, and one or more transducers, e.g., pressure sensors and flowrate sensors. The respiratory device 302 can have an electrical power supply, one or more input devices (e.g., buttons, dials, switches, touchscreens, and so on), and a central controller. In some implementations, the respiratory device 302 includes a humidifier and an anti-spill back valve that reduces risk that water will flow from the respiratory device 302 to the respirator user 104 (e.g., via the tubing 106 shown in FIG. 1).

The respiratory device 302 can further include a wired or wireless data communication interface for communicating with electronic components or sensors on the mask 201. In some implementations, the tubing 106 not only carries pressurized air but also includes an electric wire for connecting the data communication interface on the respiratory device 302 to sensors and/or one or more electronic components (e.g., sensors, speakers, microphones, cameras, memory, control systems, etc., or any combination thereof) built into and/or coupled to the mask 310.

The system 300 can further include a microphone 320 for sensing sound in its vicinity. The microphone 320 can be wired or wireless and can be positioned at any place in a room, e.g., the bedroom in FIG. 1. The microphone 320 can also be positioned somewhere on and/or in the respiratory device 302, the mask 310, or both.

The system 300 can further include a speaker 330 for generating one or more sounds. In some implementations, the speaker 330 is caused to generate sound based on sensing with the microphone 320 that air is leaking from the plenum chamber of the mask 310. The speaker 330 can generate a soothing sound, white noise, shaped white noise, pink noise, brown noise, or any other sound(s) or combination of sounds, such as those described herein.

In some implementations, the system 300 includes multiple speakers 330 to provide localized sound emission. The speakers 330 can include in the ear speakers, over the ear speakers, adjacent to the ear speakers, ear buds, ear pods, or any combination thereof. The speakers 330 can be wired or wireless speakers (e.g., headphones, bookshelf speakers, floor standing speakers, television speakers, in-wall speakers, in-ceiling speakers, etc.). In some implementations, the speakers 330 are worn by the respirator user 104 and/or the bed partner 102. In some such implementations, the provided speakers 330 can supply the masking noise without impacting the bed partner as the sound would be localized via the type of the speakers 330. In such implementations, respective localized speakers 330 could be provided for the respiration user and/or the bed partner.

In some implementations, the speaker 330 is attached to one or more of the strap segments 205a, 205b, and 205c (FIG. 2) of the mask 310. For example, the speakers can be positioned at locations 720a, 720b of the mask 701 (shown in FIG. 7). Thus, the respirator user 104 and/or the bed partner 102 has the choice to perceive a relatively flat shaped white noise sound, or for a quieter (lower level and/or low pass filtered) shaped noise signal. Some variants of the flat shaped white noise sound are referred to as pink noise, brown noise, violet noise, etc. In some such implementations, the higher frequency sounds/noises (e.g., "harsher" sounds) are reduced, while still providing masking sounds to the environmental noise. The system 300 can select an optimized set of fill-in sound frequencies to achieve a target noise profile. For example, if certain components of sound already exist in the frequency spectrum (e.g., related to a box fan in the room, a CPAP blower motor, etc.), then the system 300 can select fill-in sounds with sound parameters/characteristics that fill in the quieter frequency bands, for example, up to a target amplitude level. Thus, the system 300 is able to adaptively attenuate the higher and/or lower frequency components using active adaptive masking and/or as adaptive noise canceling such that the perceived sound is more pleasant and relaxing to the ear (the latter being more suited to more slowly varying and predictable sounds).

The speakers 330 can support an audio profile such that a wireless network interface (e.g., built into the respiratory device 302 or other smart home device) can be used to synchronize the speakers 330 with one or more other devices in the system 300.

In some implementations, in lieu of, or in addition to, using the speaker 330 to generate one or more sounds, the system 300 can use the humidification tank 309 to emit a bubbling sound, a wave sound, and/or any other water related sounds (e.g., sounds generated by the movement and/or manipulation of water). That is, the humidification tank 309, which typically stores water during use of the respiratory device 302 for humidification purposes of pressurize air delivered to the respirator user via the mask 310, can bubble and/or move the water therein to purposefully make water related sounds. The water related sounds can be used for the same reasons as the sounds generated by the speakers 330 discussed herein. In some such implementations, air is added, delivered, and/or injected into the humidification tank 309 such that the air bubbles up through the water stored therein to make bubbling sounds. Alternatively or additionally, air can be added to the humidification tank 309 to cause one or more water waves therein, thereby causing a wave sound. The air added to the humidification tank 309 can be supplied by a pump included in the respiratory device 302 used to supply the pressurized air to the mask 310 and/or by a different pump and/or fan. In some implementations, the humidification tank 309 includes one or more vents therein (e.g., on a top surface) to aid in allowing the water related sounds to exit the humidification tank 309 and be audible to the respirator user and/or the bed partner.

In some implementations, in lieu of, or in addition to, using the speaker 330 to generate one or more sounds, the system 300 can cause a deliberate leak of pressurized air to occur in the respiratory device 302 or any component of the respiratory device 302, the tube 306, the mask 310, the humidification tank 309, or any combination thereof. In some such implementations, the system 300 includes one or more valves that can be selectively actuated by the control system 390 to cause the deliberate leak of pressurized air. The one or more valves can be coupled to and/or adjacent to the tube 306, the mask 310, the humidification tank 309, the respiratory device 302, or any portion(s) thereof. The one or more valves can be controlled (e.g., opened, closed, partially opened, modulated, etc.) to shape the sound (caused by the leaking air through the one or more valves) to a desired frequency, amplitude, tone, etc. In some implementations, the deliberately leaking air causes a sound that is shaped to be white noise, pink noise, brown noise, soothing sound, etc., or any combination thereof. In some implementations, at least a portion of the one or more valves are coupled to the tube 306 and the modulation of such valves is modified by the control system 390 based at least in part on the orientation of the tube 306. Specifically, the tube 306 is flexible and can take various positions, shapes, etc. Thus, the control system 390 is configured to monitor the position/orientation of the tube 306 and/or monitor the generated sound and modify the modulation of the at least a portion of the one or more valves such that the generated sound is as intended/desired by the system 300 (e.g., to approximate or produce white noise, pink noise, brown noise, soothing sounds, etc., or any combination thereof). The position/orientation of the tube 306 can be determined by the system 300 by analyzing image data associated with the tube 306 generated by one or more cameras (e.g., camera 340, infrared camera 342, etc. or any combination thereof).

As noted above, the respiratory device 108, 302 generates pressurized air and the normal operating of the respiratory device 108, 302 can, in some instances, cause noise that the system 300 mitigates by the generation of one or more sounds (e.g., soothing sounds, white noise, pink noise, brown noise, etc., or any combination thereof). In some implementations, an orientation and/or placement of the respiratory device 108, 302 on specific surfaces (nights stand, table, floor, etc.) and/or objects and/or near specific objects, can cause and/or contribute to the respiratory device 108, 302 and/or one of its components (e.g., blower motor, etc.) generating a noise that is perceived as being unpleasant to the respirator user and/or the bed partner. Further, in some implementations, the generated noise can develop and/or intensify overtime due to, for example, normal wear and tear of the respiratory device 108, 302 and/or the placement of the respiratory device 108, 302. In some such implementations, the system 300 can generate the masking sounds described herein to mitigate and/or obscure such noises.

The system 340 can further include a camera 340, an infrared camera 342, a pressure sensor 350, a motion sensor 355, and other sensors 360 (e.g., an electrocardiogram (EKG) sensor, an electroencephalography (EEG) sensor, an electromyography (EMG) sensor, a blood flow sensor, a respiration sensor, a pulse sensor, a photoplethysmogram (PPG) sensor, an oxygen sensor, an analyte sensor, a moisture sensor, a LiDAR sensor, etc.). The camera 340 and infrared camera 342 can be positioned to capture movement and change in heat signatures of the respirator user 104 and/or the bed partner 102. The pressure sensor 350 can be located anywhere along the air circuit from the respiratory device 302 to the mask 310. The pressure sensor 350 can be multiple pressure sensors positioned along the air circuit to measure pressure at different points within the air circuit (e.g., at the plenum chamber of the mask, along the tubing connecting the mask to the respiratory device, at either end of the tubing, at the respiratory device, and so on).

The motion sensor 355 can detect movement of the respirator user 104 and/or the bed partner 102. In some implementations, the motion sensor 355 cooperates with the infrared camera 342 to determine changes and/or shifts in body temperature with respect to ambient temperature to determine whether a person is moving. In some implementations, the motion sensor 355 utilizes electromagnetic sensing in the infrared wavelength for detecting motion and determines that body temperature slightly falls while an individual is sleeping so when body temperature rises above a certain level based on infrared sensing, then the motion sensor 355 determines that the individual is waking up and moving. Other examples of the motion sensor 355 include passive infrared sensors, radio frequency sensors such as pulsed continuous wave (CW) sensors, ultrawideband (UWB) sensors, frequency modulated continuous wave (FMCW) sensors, sensors that emit ultrasonic signals and determine whether detected reception of reflected ultrasonic signals indicate a changing pattern, gyroscopes and accelerometers embedded in pajamas or beddings, etc., or any combination thereof.

The memory 380 can include one or more physically separate memory devices, such that one or more memory devices can be coupled to and/or built into the respiratory device 302, the control system 390, and/or one or more external devices (e.g., mobile phones, computers, servers, cloud based devices, etc.) wirelessly coupled and/or wired to the system 300. The memory 380 acts as a non-transitory computer readable storage medium on which is stored machine-readable instructions that can be executed by the control system 390 and/or one or more other systems. The memory 380 is also able to store (temporarily and/or permanently) the data generated by sensors of the system 300. In some implementations, the memory 380 includes non-volatile memory, battery powered static RAM, volatile RAM, EEPROM memory, NAND flash memory, or any combination thereof. In some implementations, the memory 380 is a removable form of memory (e.g., a memory card).

Like the memory 380, the network interface 370 can be coupled to the respiratory device 302, the mask 310, the control system 390, and/or one or more external devices. The network interface 370 is coupled to the memory 380 such that the control system 390 is configured to communicate with one or more external devices or other components in the system 300.

Also like the memory 380, the control system 390 can be coupled to the respiratory device 302, the mask 310, and/or one or more external devices. The control system 390 is coupled to the memory 380 such that the control system 390 is configured to execute the machine-readable instructions stored in the memory 380. The control system 390 can include one or more processors and/or one or more controllers. In some implementations, the one or more processors includes one or more x86 INTEL processors, one or more processors based on ARM® Cortex®-M processor from ARM Holdings such as an STM32 series microcontroller from ST MICROELECTRONIC, or any combination thereof. In some implementations, the one or more processors include a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS.

In some implementations, the control system 390 is a dedicated electronic circuit. In some implementations, the control system 390 is an application-specific integrated circuit. In some implementations, the control system 390 includes discrete electronic components.

The control system 390 is able to receive input(s) (e.g., signals, generated data, instructions, etc.) from any of the other elements of the system 300 (e.g., the sensors, etc.). The control system 390 is able to provide output signal(s) to cause one or more actions to occur in the system 300 (e.g., to cause the speaker 330 play a sound, etc.).

While the control system 390 and the memory 380 are described and shown in FIG. 3 as being a separate and distinct component of the system 300, in some implementations, the control system 390 and/or the memory 380 are integrated in the respiratory device 302. Alternatively, in some implementations, the control system 390 or a portion thereof (e.g., at least one processor of the control system 390) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While the system 300 is shown as including all of the components described above, more or fewer components can be included in a system for generating data and determining a recommended notification or action for the user according to implementations of the present disclosure. For example, a first alternative system includes the control system 390, the memory 380, and at least one of the sensors provided in FIG. 3. As another example, a second alternative system includes the control system 390, the memory 380, the respiratory system 302, and at least one of the sensors provided in FIG. 3. Thus, various systems can be formed using any portion or portions of the components shown and described herein and/or in combination with one or more other components.

As used throughout the present disclosure, the term leak is understood to be an unintended flow of air from the system 300 to ambient. For example, a leak may occur as the result of an incomplete seal between the mask 310 and the face of the respirator user 104. In another example, a leak may occur in a swivel elbow (e.g., connection port 212 in FIG. 2) or connection anywhere in the air circuit of the system 300 to ambient. In some implementations, the mask 310 includes the connection section 210 (FIG. 2) which includes vents designed to allow exhaled gases to escape the plenum chamber 202. The gases escaping the plenum chamber 202 via the vents are not considered leaks because the gases comprise intended flow within the system 300. In some implementations, the air flowing through the vents of the system 300 can be referred to as permitted leaks.

Figure 4:
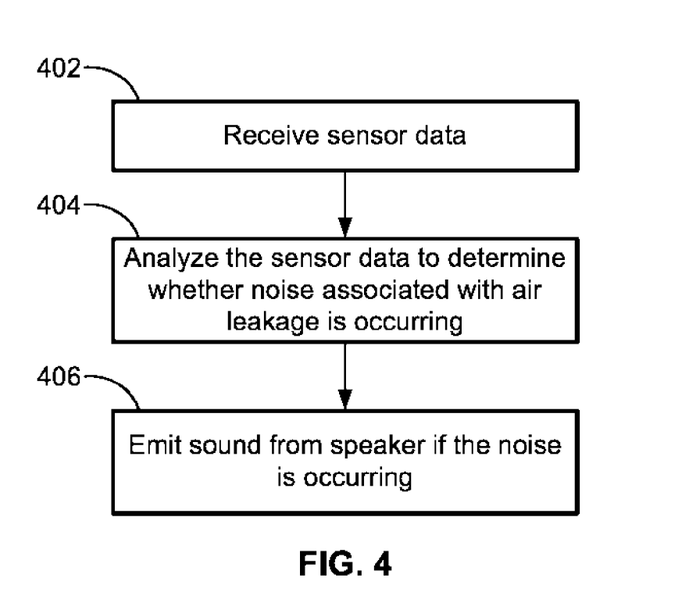
FIG. 4 is a flow diagram for generating sound from a speaker to respond to noise from a respiratory system and/or its components, according to some implementations of the present disclosure.

Referring to FIG. 4, a flow diagram illustrating a method for generating sound from the speaker 330 to respond to noise from the system 300 (e.g., from the respiratory device 302, air leaking from the mask 310, etc., or any combination thereof) is shown according to some implementations of the present disclosure. At step 402, the control system 390 (and/or the respiratory device 302 in some implementations) receives sensor data. The sensor data can come from the microphone 320 generating sound data (or audio data) while the respirator user 104 is asleep. In some implementations, the sensor data comes from one or more of the microphones 320, one or more of the pressure sensors 350, one or more of the infrared cameras 342, one or more of the cameras 340 and/or one or more of the other sensors 360, one or more flow rate sensors, or any combination thereof.

At step 404, the control system 390 analyzes the sensor data to determine whether noise associated with air leakage in the system 300 is presently occurring. In some implementations where a microphone is not used to determine air leakage, an assumption can be made that air leakage detected (e.g., by the respiratory device 302) produces a sound. For example, if the control system 390 is embedded in the respiratory device 302, the respiratory device 302 can determine through pressure measurements and analysis of data using one or more algorithms that air is presently leaking.

In some implementations, the control system 390 determines and/or measures one or more flow rates to aid in determining whether air leakage is occurring. The control system 390 can determine flow rate of the respiratory device 302, which is the flow rate of air leaving the respiratory device 302. The control system 390 can further determine a total flow rate reaching the mask 310 via the air circuit, where the total flow rate is the flow rate of air and any supplementary gas introduced via any supplementary port of the mask 310 that reaches the mask 310 via the air circuit. The control system 390 can determine a vent flow rate, which is the flow rate of air leaving a vent to allow washout of exhaled gases. The control system 390 can further determine a leak flow rate, which is the flow rate of leak from the mask 310 and/or anywhere else on the air circuit. The control system 390 can also determine a respiratory flow rate, which is the flow rate of air that is received into the respiratory system of the respirator user 104.

In some implementations, the control system 390 can determine pressure at the mask 310, the respiratory flow rate, and the leak flow rate using pressure sensors and/or one or more flow rate sensors. The control system 390 can further estimate leak flow rate and respiratory flow rate.

In some implementations, the control system 390 determines pressure at the mask 310 using the pressure sensors 350 and/or one or more flow rate sensors. The pressure sensor 350 can provide pressure leaving the respiratory device 302 and the flow rate sensors can provide flow rate of air leaving the respiratory device 302. The control system 390 can then use the pressure leaving the respiratory device 302 to estimate a drop in pressure throughout the air circuit and/or one or more portions thereof. Absent any supplementary gases introduced to the mask 310, the flow rate of the respiratory device 302 can be used as an estimate of the total flow rate reaching the mask 310.

In some implementations, the control system 390 can model the dependence of the pressure drop through the air circuit on the total flow rate reaching the mask 310 for particular air circuits to determine pressure characteristics. The control system 390 can then use the pressure characteristics to determine an estimated pressure reaching the mask 310. For example, pressure reaching the mask 310 can be determined as respiratory device pressure minus the air circuit pressure drop.

In some implementations, the control system 390 determines vent flow rate using the pressure reaching the mask 310 and estimates the vent flow rate in the mask 310. Dependence of the vent flow rate on the pressure reaching the mask 310 can be modeled apriori, and the control system 390 uses the modeled characteristic to determine particular vent flow rates for particular determined pressures reaching the mask 310.

In some implementations, the control system 390 estimates leak flow rate via the total flow rate and the vent flow rate. The leak flow rate can be estimated by the control system 390 by calculating an average of the difference between total flow rate and vent flow rate over a period sufficiently long to include several breathing cycles. The period can be, for example, 5 second, 10 seconds, 20 seconds, 30 seconds, etc.

In some implementations, the control system 390 estimates leak flow rate via the total flow rate, the vent flow rate, and the estimated pressure reaching the mask 310. The leak flow rate can be estimated by calculating a leak conductance and determining the leak flow rate to be a function of the leak conductance and the estimated pressure reaching the mask 310. The leak conductance can be calculated as the quotient of a low-pass filtered non-vent flow rate equal to the difference between total flow rate and vent flow rate and low-pass filtered square root of the pressure reaching the mask 310, where the low pass filter time constant has a value sufficiently long to include several breathing cycles. The breathing cycles can last for about 10 seconds, 20 seconds, etc. The leak flow rate can be estimated as the product of the leak conductance and a function of the pressure reaching the mask 310.

In some implementations, the control system 390 estimates the respiratory flow rate via the total flow rate, the vent flow rate, and the leak flow rate. The respiratory flow rate can be determined by subtracting the vent flow rate and the leak flow rate from the total flow rate.

In some implementations, the microphone 320 provides sound data (or audio data) in step 402 to the control system 390 that is analyzed in step 404. At the beginning of a sleeping session, the microphone 320 can provide an ambient noise level to the control system 390, and during the sleeping session, if the noise in the bedroom reaches a threshold above the ambient noise level, then the control system 390 determines that there is air leakage. The ambient noise level at the beginning of the sleep session is established, e.g., 10 seconds, 30 seconds, 2 minutes, etc., after the respirator user 104 turns on the respiratory device 302.

In some implementations, the control system 390 analyzes the noise picked up by the microphone 320 to determine a profile of the noise. If the noise has certain frequency and/or amplitude characteristics similar to quickly moving air, then the control system 390 increases confidence that the noise is associated with air leaking from the air circuit of the system 300. On the other hand, if the frequency and/or amplitude characteristics indicate a siren or some other noise with a fleeting frequency and/or amplitude characteristic, then although the noise is above the threshold, the control system 390 determines that air leakage is not present.

In some implementations, the microphone 320 represents more than one microphone arranged in several locations (e.g., two locations, three locations, five locations, etc.) throughout the bedroom or room. Using the positioning of the different microphones, an origination location of sound can be determined such that when the noise threshold is reached, the arrangement of microphones can be used to determine whether the extra sound adding to the noise level is coming from an area around the bed or from somewhere else, for example, a pipe routed above the ceiling. The control system 390 can determine with greater confidence that the noise is associated with air leakage if the sound is deemed to be coming from a location close to where the respirator user 104 and/or the system 300 is located. Although described with respect to multiple microphones, one microphone positioned close to the bed, positioned in and/or on the respiratory device 302, positioned in and/or on the mask 310, or any combination thereof, can be used to improve confidence that the sound data above and/or meeting a certain threshold indicates air leakage in the system 300. Since sound decays as it moves away from its source, placing the microphone 320 on the respiratory device 302 or on the mask 310 or close to the bed can allow better monitoring of sound within the vicinity of the respirator user 104 during the sleeping session.

In some implementations, infrared data can be combined with sound data (or audio data) to determine whether there is a change in heat around the respirator user 104 in order to increase confidence that noise associated with air leakage is occurring. Since the pressurized air coming from the respiratory device 302 can be heated so that the respirator user 104 is not breathing in cold air that can disturb her sleep, when a leak occurs, there can be a change in heat around the respirator user 104 as heated air escapes the air circuit of the system 300.

In some implementations, infrared data alone can be used without the sound data to determine whether air leakage is presently occurring (e.g., from the interface of the mask 310 with the face of the respirator user 104). The control system 390 can analyze infrared data from the infrared camera 342 to identify positions of the respiratory device 302, the mask 310, and the air circuit shared between the respiratory device 302 and the mask 310. The infrared data analyzed can be marked as a baseline infrared data for comparison. During a sleeping session, if air leakage occurs, heated pressurized air will escape causing a disturbance of the infrared imaging, and a second infrared data set received at the control system 390 can be compared against the baseline infrared data set to determine whether air leakage has occurred.

In some implementations, motion data from the motion sensor 355 is combined with infrared data to reduce the amount of computation carried out by the control system 390. Changes in infrared data can occur over time since individuals are prone to moving and changing positions while asleep. To reduce constant comparisons of imaging data to determine whether air leakage has occurred, motion data is first analyzed to determine whether the respirator user 104 has moved. If the respirator user 104 moved, then a direction of motion is combined by the control system 390 to analyze a specific portion of the infrared data to determine whether the movement of the respirator user 104 alone can account for a change in the infrared data. If the movement alone does not account for the change in infrared data, then the control system 390 determines that air leakage might be the culprit.

At step 406, in response to determining that the noise is from air leakage that is presently occurring, the control system 390 causes the speaker 330 to emit a sound. The sound emitted from the speaker can be used to mask the noise associated with air leaking from the air circuit of system 300, for example, from the mask 310, the tubing connecting the respiratory device 302, etc. The control system 390 can cause the speaker 330 to emit the sound at a first volume and then incrementally increase the volume from the first volume to a second louder volume over a period of time. For example, the speaker 330 can emit sound at a relatively low volume initially then gradually increase the volume so as to not wake and/or disturb the respirator user 104 and/or the bed partner 102 with a sudden introduction of a new sound. The time period for the ramping up the volume can be 1 second, 5 seconds, 10 seconds, 20 seconds, 30 seconds, etc. or any other amount of time.

In some implementations, the control system 390 can cause the speaker 330 to emit the sound at a first volume when the respiration user and/or the bed partner are first going to sleep or in a first type of sleep state (e.g., in light sleep stages, NREM, N1, N2, etc.) and at a second volume when the respiration user and/or bed partner are asleep or in a second type of sleep state (e.g., in REM, N3, slow wave sleep (SWS), etc.). In some such implementations, the first volume is greater than the second volume. As such, any noise generated by the respiratory device 302 and/or air leaks and/or other noise is less likely to disturb the respirator user and/or bed partner when going to sleep. Similarly, the relatively lower volume of the sound when the respirator user and/or bed partner are sleeping and/or in REM sleep is less likely to disturb (e.g., wake-up) the respirator user and/or bed partner. The different volumes for the emitted sound can be appropriate for urban environments and/or for bed partners and/or respirator users that are relatively more sensitive to noise when falling asleep. In situations where the respirator user and/or bed partner fall asleep relatively quickly and are less bothered by noise during this time, a relatively lower volume for the emitted sound can be used by the system 300.

In some implementations, the speaker 330 is located in a pillow on the bed, so the sound can be emitted at a lower volume than if the speaker 330 were located farther from the respirator user 104. The sound emitted can be white noise and/or a soothing sound. The soothing sound can include beach sounds, bird sounds, waterfall sounds, running water sounds, wind sounds, or any combination thereof.

In some implementations, responsive to the analysis at step 402 resulting in a determination that noise associated with air leaking from the air circuit of the system 300 is not occurring and/or the respiratory device 302 determining that air is not leaking from the air circuit, the system 300 causes the speaker 330 to emit the sound at a first volume during the sleep session. Emitting a sound by the speaker 330 at the first volume when air leakage is not detected can allow the speaker to set the ambient noise level so that when air leakage is detected at step 404, then the speaker 330 can emit the sound at a relatively higher volume level to mask the sound of the noise associated with the air leakage.

In some implementations, the noise associated with the air leakage can be a temporary phenomenon. For example, the respirator user 104 can change positions while sleeping so that in a first position, no air leakage is occurring as the respirator user 104 is lying on her back, and in a second position, air leakage occurs creating an associated noise. When the respirator user 104 moves from the first position to the second position, air leakage and an associated noise occurs, and when the respirator user 104 moves from the second positon back to the first position, then air leakage and the associated noise does not occur. This temporary phenomenon can be monitored and the system 300 can respond differently. For example, if the respirator user 104 moves frequently such that air leaks for a relatively short period of time causing an associated noise that lasts for a short period of time (e.g., less than 10 seconds), the system 300, in some such implementations, may not cause the speaker 330 to emit sound in response thereto (e.g., as frequent on/off of the sound itself may be disruptive to the bed partner 102 and/or the respirator user 104).

In some implementations, responsive to the speaker 330 being caused to start emitting the sound, the control system 390 continues to analyze the sensor data to determine if noise associated with air leaking from the mask is still occurring. The control system 390 can examine the characteristics of the sound coming from the speaker 330 and separate that from the characteristics of the sound in the room. From the sound in the room, the control system 390 determines that the noise is still occurring so the control system 390 allows the speaker 330 to continue emitting sound. When the control system 390 determines that the sound is no longer occurring, the control system 390 can cause the speaker to stop emitting the sound. In some implementations, as the respirator user 104 changes position while sleeping, thus affecting whether or not the air circuit of the system 300 leaks, the control system 390 causes the speaker 330 to emit a sound or to stop emitting a sound. In some implementations, the control system 390 causes the speaker 330 to emit a sound at a lower volume when no air leakage is detected and a sound at a higher volume when air leakage is detected.

In some implementations, to minimize the intrusion of the sound from the speaker 330 cutting in and out too frequently during a sleeping session, the control system 390 utilizes a minimum duration that the speaker 330 will emit a sound. That is, once the speaker 330 starts emitting a sound, then it must continue for a minimum duration before the control system 390 causes the speaker 330 to stop emitting the sound. The minimum duration can be preprogrammed or can be determined based on a disturbance level of the respirator user 104 or the bed partner 102 when the sound is first emitted by the speaker 330. The minimum duration can change over the course of the sleeping session or multiple sleep sessions based on an adaptive sensing of the previous disturbances of previous times sound was generated during the sleeping session. The minimum duration can be, for example, 10 seconds, 20 seconds, 30 seconds, 1 minute, 2 minutes, 5 minutes, 30 minutes, etc. or any other length of time.

In one example of the present disclosure, the control system 390 determines that noise associated with air leakage is occurring and then causes the speaker 330 to emit a sound, and the minimum duration for playing the sound is 30 seconds (in this example). Ten seconds later, the control system 390 determines that the noise is no longer occurring. In such an example, the control system 390 then instructs the speaker 330 to stop playing the sound at the 30 second mark (assuming that a new noise is not detected in the interim). As such, the minimum duration of 30 seconds for the sound to be emitted is met.

In another example of the present disclosure, the control system 390 determines that noise associated with air leakage is occurring and then causes the speaker 330 to emit a sound, and the minimum duration for playing the sound is 30 seconds. Forty seconds later, the control system 390 determines that the noise is no longer occurring. In such an example, the control system 390 instructs the speaker to stop playing the sound immediately as the minimum duration of 30 seconds of playing the sound has already been met.

In some implementations, the control system 390 determines and/or estimates one or more leak flow rates using one or more algorithms. The leak flow rates can be used to determine whether to emit the sound. For example, in some implementations, if the determined leak flow rate is above a threshold level (e.g., above 5 liters of air per minute, above 10 liters of air per minute, above 15 liters of air per minute, above 20 liters of air per minute, above 24 liters of air per minute, above 30 liters of air per minute, above 40 liters of air per minute, etc., or any other threshold level), the control system 390 causes the speaker 330 to emit the sound. In some such implementations, the sound is only emitted after the control system 390 also determines that a noise associated with the leak is presently occurring. In some such implementations, the sound is only emitted after the control system 390 also determines that the respirator user 104 and/or the bed partner 102 are present.

In some implementations, in addition to causing the sound to be emitted when a leak is detected and/or otherwise determined to be presently occurring, when a leak flow rate is determined that exceeded an alarm threshold, the control system 390 can cause an alarm and/or an alert to be generated. Such alarm or alert can notify the respirator user 104, the prescribing doctor, or any other third party or parties that the respiratory device 302, the mask 310, and/or any component of the air circuit should be serviced, replaced, or otherwise attended to. In such implementations, when the leak flow rate is below the alarm threshold, the control system 390 causes the speaker 330 to emit a sound without generating the alarm and/or alert. In some such implementations, the alarm threshold is 20 liters of air per minute, 24 liters of air per minute, 30 liters of air per minute, etc. or any other threshold amount.

Figure 5:
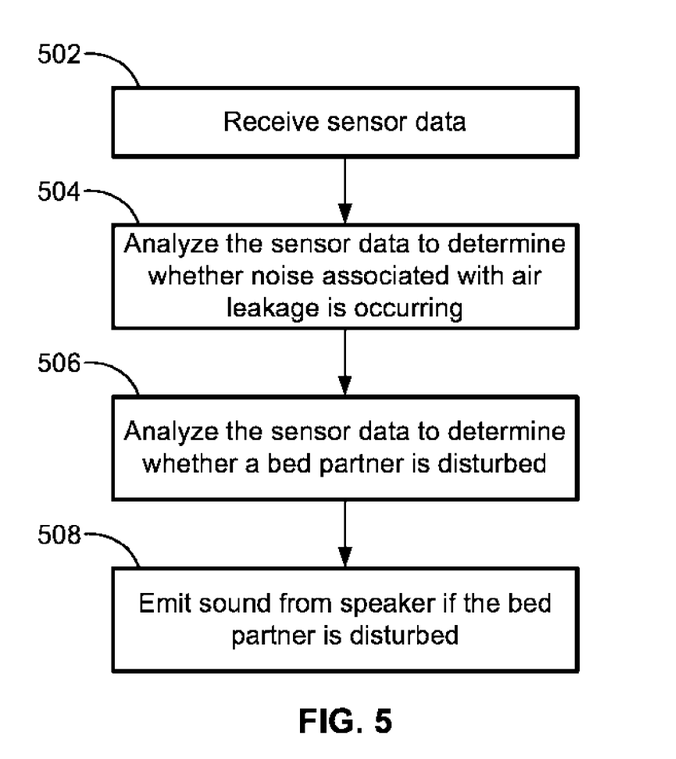
FIG. 5 is a flow diagram for generating sound from a speaker to respond to noise from a respiratory system and/or its components, according to some implementations of the present disclosure.

FIG. 5 is a flow diagram illustrating a method for generating sound from the speaker 330 to respond to noise from the system 300 (e.g., from the respiratory device 302, air leaking from the mask 310, etc., or any combination thereof) shown according to some implementations of the present disclosure. At step 502, the control system 390 (and/or the respiratory device 302 in some implementations) receives sensor data. At step 504, the control system 390 analyzes the sensor data to determine whether noise associated with air leakage is presently occurring. Steps 502 and 504 are the same as, or similar to, steps 402 and 404 described above in connection with FIG. 4.

At step 506, the control system 390 analyzes the sensor data to determine whether a bed partner, (e.g., the bed partner 102 shown in FIG. 1), is disturbed. In some implementations, the control system 390 uses sound data from the microphone 320 to determine whether the bed partner 102 is disturbed. The control system 390 can use the sound data from the microphone 320 to determine that the sleep stage of the bed partner 102 has changed, and thus, determine that the bed partner 102 is being disturbed.

In some implementations, the control system 390 uses the motion sensor 355, the microphone 320, the camera 340, the infrared camera 342, or any combination thereof to determine that the bed partner 102 is moving, and from the movement of the bed partner 102, determine that the bed partner 102 is disturbed. The motion sensor 355 can use electromagnetics signals, (e.g., an RF signal) to determine movement of the bed partner 102.

In some implementations, the control system 390 uses the microphone 320 and the speaker 330 to determine that the bed partner 102 is moving by generating an inaudible sound with the speaker 330 and sensing the reflection of the inaudible soundwave with the microphone 320 over a period of time. The change in the reflection of the inaudible soundwave over the period of time can be used to determine whether the bed partner 102 is moving, and if the bed partner 102 is moving, then the control system 390 determines that the bed partner 102 is disturbed.

In some implementations, the microphone 320 can generate sound data that is analyzed by the control system 390 to determine breathing patterns of the bed partner 102 to determine a sleep stage of the bed partner 102. If the sleep stage of the bed partner 102 changes, then the control system 390 determines that the bed partner is disturbed.

In some implementations, the movement of the bed partner 102 is detected via rustling of the bedding caused by the movement of the bed partner, the bed partner starting to snore, the bed partner speaking, the bed partner sighing, or any combination thereof.

In some implementations, the control system 390 can determine a confidence level in the disturbance of the bed partner. The confidence level can range from a score of 0 to 10 where 10 indicates highest level of disturbance and 0 indicates no disturbance. Different examples of bed partner movements can be placed in this confidence level scoring. Detection of a change in sleep cycle can be on the lower end of the confidence level scoring. Whereas detection of the bed partner 102 sighing and/or talking can be on the higher end of the confidence level scoring.

At step 508, based on the bed partner 102 being disturbed by the detected noise associated with the air leakage, the control system 390 causes the speaker 330 to emit a sound. Several implementations described above under step 406 equally apply to step 508 and are not repeated here.

In some implementations, the control system 390 selects the sound emitted by the speaker 330 based on the confidence level scoring. For example, white noise can be emitted from the speaker 330 for a confidence level score of 2 while classical music can be emitted at a confidence level of 5. In another example, more than two options are available where different sounds can be turned to at different confidence levels.

In some implementations, the control system 390 selects the sound emitted by the speaker 330 based on a profile of the respirator user and/or a profile of the bed partner. In such implementations, the respirator user and/or the bed partner can setup and/or establish a user profile for the system 300 that includes, among other things, a preference for sounds to be played to obscure noises of the respiratory device 302 and/or mask leaks. Further, the profile for the respirator user can include historical data related to volumes of noises and/or sounds that the system 300 mitigates. As such, the system 300 is able to compare current noises/sounds with historical noises/sounds. Such a comparison of current and historical data can be used to determine if the noise associated with, for example, an air leak, is associated with an air leak that can simply be addressed by generating a masking sound as compared to an air leak that might be indicative of something more serious that should be addressed by, for example, replacing one or more components (e.g., a new mask, a new respiratory device, etc.) and/or by having one or more components serviced.

In some implementations, the control system 390 adjusts or sets the volume of the sound emitted by the speaker 330 based on the confidence level scoring. For example, a relatively low confidence level score (e.g., a confidence level score of 1) causes the control system 390 to have the speaker emit sound at a relatively low volume (e.g., volume of 15 out of 100) while a relatively high confidence level score (e.g., a confidence level score of 8) causes the control system 390 to have the speaker emit sound at a relatively high volume (e.g., volume of 75 out of 100). More than two options are available where different volumes can be turned on at different confidence levels. In some implementations, the control system 390 adjusts or sets the length of time the sound is emitted based on the confidence level score in a similar manner. Different confidence level scores can indicate different lengths associated with the sound emission from the speaker 330.

In some implementations where the speaker 330 emits white noise, the control system 390 can select different types of white noise or the type of white noise emitted can be preprogrammed. The control system 390 can also monitor the bed partner 102 and/or the respirator user 104 over time to determine which sound and/or white noise works best for the bed partner 102 and/or the respirator user 104. This can be achieved by monitoring a confidence level score for one or both of the bed partner 102 and the respirator user 104. The control system 390 can store in the memory 380 profiles of how the confidence level score changed in response to a certain sound and/or white noise. The emitted sound and/or white noise that historically caused the greatest drop in the confidence level score can then be selected as the one to use by the control system 390. Although discussed in terms of white noise, the sound emitted from the speaker 330 can be of any example previously described, hence a profile can be made for how, for example, beach sounds affect the confidence level scores, and so on.

In some implementations, the control system 390 can cause the speaker 330 to emit different sounds based on the sleep cycle and/or sleep stage of the respirator user 104 and/or the bed partner 102. For example, if both the respirator user 104 and the bed partner 102 are in REM sleep, no sound is emitted for type 1 leaks (e.g., short ones that last less than 20 seconds). If both are in REM sleep, sound is emitted for type 2 leaks (e.g., leaks that last longer than 20 seconds). If the bed partner 102 is not in REM sleep, then sound is emitted for all leaks. In some implementations, the determination of whether the leak is a type 1 leak or a type 2 leak can be performed dynamically. Once the control system 390 determines that there is a leak, then the control system 390 places the leak in the type 1 category by default and calculates and/or estimates how long the leak has lasted or is expected to last. If the counter or clock that the control system 390 relies upon reaches the threshold mark, e.g., 20 seconds, then the leak is re-categorized as a type 2 leak.

In some implementations, the control system 390 can determine from the sensor data whether the respirator user 104 or the bed partner 102 is awake and then cause the speaker 330 to emit a sound based on who is awake in the bedroom. In an example, the bed partner 102 goes to bed first and the speaker 330 plays a first sound. Later on, the respirator user 104 goes to bed, and the control system 390 determines that the respirator user 104 is going to bed and then causes the speaker 330 to stop playing the first sound and to start playing a second sound. In some implementations, the control system 390 determines that the respirator user 104 is going to bed by detecting via the microphone 320 and/or by the respiratory device 302 itself that the respiratory device 302 has been turned on.

In an example, the bed partner 102 goes to bed after the respirator user 104, and the control system 390, using video data from the camera 340 or heat data from the infrared camera 342, senses this sequence and causes the speaker 330 to emit the second sound. Although the description mentions a first sound and a second sound, this can be extended to a first volume and a second volume, playing no sound initially to playing a sound afterward, and combinations thereof. Further, although the description mentions a first sound is played, this also extends to mean that the first sound is played when a leak is detected and/or when the bed partner is disturbed.

Figure 6:
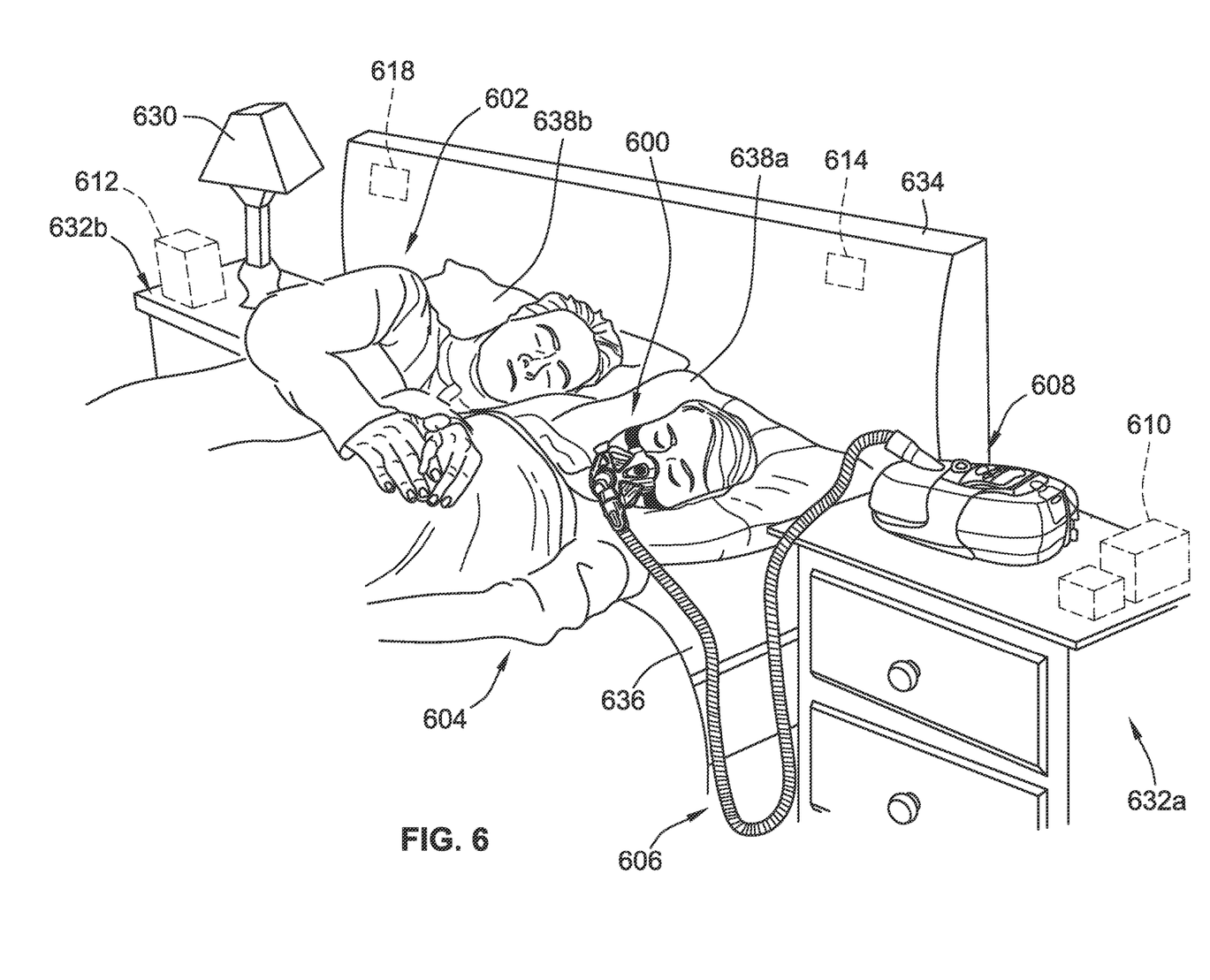
FIG. 6 illustrates an example placement of components for mitigating noise from a respiratory system and/or its components in a bedroom setting, according to some implementations of the present disclosure.

Referring to FIG. 6, an example placement of components for mitigating effects of noise from the respiratory device 608, air leaking from the mask 600, etc., or any combination thereof in a bedroom setting, is shown according to some implementations of the present disclosure. The environment is a bedroom setting that includes a respirator user 604, a bed partner 602, a bed with a mattress 636, pillows 638a and 638b, and headboard 634. Next to the bed are two nightstands 632a and 632b, and a lamp 630 on nightstand 632b. The respirator user 604 is wearing the mask 600 connected via an air circuit or tubing 606 to the respirator 608. A speaker can be placed at position 610, cameras and/or microphones can be placed at positions 618 and 614. A microphone and/or camera can be placed at position 612 to monitor, for example, the bed partner 602. Various other locations for the components are contemplated. For example, one or more cameras can be mounted in a ceiling of the room. One or more microphones can be mounted to the headboard 634 and/or a wall of the room, etc.

Figure 7:
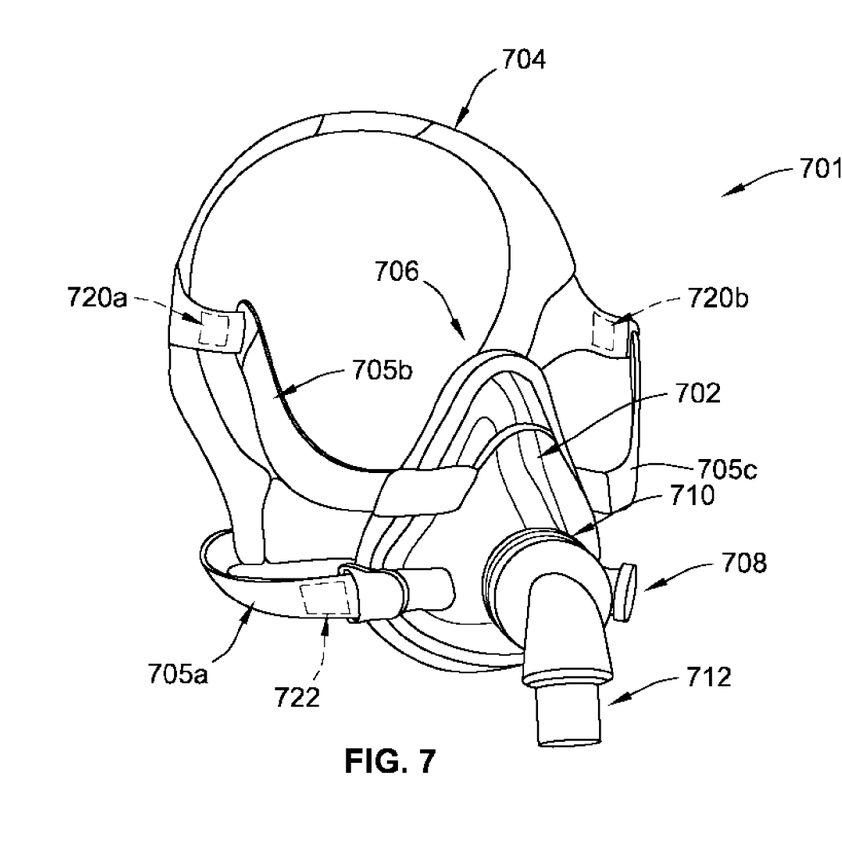
FIG. 7 illustrates a perspective view of a mask or mask assembly that can be used with a respirator to mitigate effects of noise from the respiratory system and/or its components, according to some implementations of the present disclosure.

Referring to FIG. 7, a perspective view of a mask 701 that can be used with a respirator (e.g., the respiratory device 608) to mitigate effects of noise from the respirator is shown according to some implementations of the present disclosure. The mask 701 is the same as, or similar to, the mask 201 of FIG. 2. The mask 701 includes a plenum chamber 702, a positioning or stabilizing structure 704 with strap segments 705a, 705b, and 705c, a cushion 706, an electronics interface 708, a connecting section 710, and a connection port 712. The mask 701 can include several locations for embedding sensors. For example, sensors or the like can be positioned at positions 720a, 720b, and/or 722. Such sensors can include a microphone embedded in the mask for use in determining air leakage. Further, one or more speakers can be included at the positions 720a, 720b, and/or 722 for emitting sounds.

While the above disclosure generally discusses the use of sounds (e.g., white noise, pink noise, brown noise, soothing sounds, etc.) to aid in masking noises from, for example, air leaks at a mask interface of a respiratory system, respiration device sounds, etc., it is contemplated that the same, or similar, sounds can be used to train and/or guide a respiration user's breathing (e.g., when trying to fall asleep). The training and/or guiding of a respiration user's breathing while receiving pressurized air therapy and trying to fall asleep can aid respiration users in relaxing when trying fall asleep and/or adopting the pressurized air therapy. The breathing training can be provided by sounds (e.g., white noise, shaped white noise, modulated sounds such as, for example, wave sounds, etc.) to encourage the respiration user to entrain their breathing to the guiding modulation (e.g., to help the respiration user relax and ultimately fall asleep). In some implementations, the provided sounds can help guide the respiration user to lower their breathing rate and to take deeper breaths, which can help the respiration user to fall asleep. In some implementations, the provided sounds can aid the respiration user in exhaling at a relatively slowly rate than inhaling. In some implementations, the provided sounds can aid the respiration user in controlling their breath hold time to be a time between an exhale and inhale time. In some implementations, the provided sounds can be linked to and/or tied with a ramp setting of the respiration system to better optimize an overall pressurized air therapy during the going to sleep portion of a sleep session of the respiration user. That is, in some implementations, the pressure setting of the pressurized air supplied to a respiration user can be ramped up or increased over time while the respiration user is trying to fall asleep and the sounds that are played to aid in relaxing and breath control can be played for the same, or similar, period of time. The length of the period of time that the respiration user needs to fall asleep can be learned overtime and the ramp settings and/or sound settings can be customized over time based at least in part on data gathered during use of the respiration system with the sound feature.

In some implementations, the room where the respiration system is used includes a natural source of noise and/or sounds that are the same as, or similar to, white noise, pink noise, brown noise, etc., or any combination thereof. For example, the room may include and/or be adjacent to a desk fan, a box fan, a window fan, a ceiling fan, a furnace, an air conditioner, a washing machine, a dryer, an electrical device producing an electrical hum, etc. Each of these existing sources of sounds can be supplemented by the systems of the present disclosure to fill in and/or complement the existing sounds with additional sounds. In some such implementations, the existing sounds have existing sound characteristics, which can be sensed by the system (e.g., by one or more sensors of the system, such as, for example one or more microphones, one or more transducers, etc.). The existing sound characteristics can include a frequency, an amplitude, a period, a wavelength, a velocity of wave, a pitch, dynamics, tone, timbre, duration, envelope, location, or any combination thereof. The system can complement the existing sounds with intermediate sounds/complementary sounds that have complementary sound characteristics. For example, the complementary sounds can have frequencies and/or amplitudes, etc. that are between the frequencies and/or amplitudes of the existing frequencies and/or existing amplitudes. As such, the overall sound (e.g., including the existing sounds and the complementary sounds of the system of the present disclosure) can provide a relatively fuller sound to mask noises.

One or more elements or aspects or steps, or any portion(s) thereof, from one or more of any of claims 1-75 below can be combined with one or more elements or aspects or steps, or any portion(s) thereof, from one or more of any of the other claims 1-75 or combinations thereof, to form one or more additional implementations and/or claims of the present disclosure.

While the present disclosure has been described with reference to one or more particular implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:

1. A method comprising:
receiving first audio data from a first microphone;
receiving second audio data from a second microphone;
analyzing the first audio data to determine if noise associated with air leaking from a mask is occurring, the mask being coupled to a respiratory device supplying pressurized air, the mask being configured to engage a user during a sleep session to aid in directing the supplied pressurized air to an airway of the user;
responsive to (i) the analysis of the first audio data resulting in a determination that noise associated with air leaking from the mask is occurring, or (ii) the respiratory device determining that air is leaking from the mask, or (iii) both (i) and (ii), further analyzing the second audio data to determine if a bed partner of the user is presently disturbed, and
causing a speaker to emit sound based on the further analysis of the second audio data resulting in a determination that the bed partner is presently disturbed, wherein the emitted sound aids in masking the noise associated with the air leaking from the mask.

2. The method of claim 1, wherein the analysis of the second audio data includes determining if a sleep stage of the bed partner has changed.

3. The method of claim 1, further comprising receiving motion data from one or more sensors, wherein the second audio data, the motion data, or both are analyzed to determine if the bed partner is presently disturbed, and wherein the second audio data, the motion data, or both are indicative of movement of the bed partner, rustling of bedding caused by movement of the bed partner, a change in breathing of the bed partner, a change in sleep stage of the bed partner, the bed partner starting to snore, the bed partner speaking, the bed partner sighing, or any combination thereof.

4. The method of claim 1, wherein the analysis of the second audio data includes determining a disturbance score for the bed partner, the disturbance score indicating a level of disturbance of the bed partner.

5. The method of claim 4, wherein the disturbance score is a number between 0 and 10, where 0 indicates no disturbance and 10 indicates the highest level of disturbance.

6. The method of claim 4, wherein the emitted sound is selected from a plurality of sounds based at least in part on the determined disturbance score.

7. The method of claim 4, wherein a volume of the emitted sound, a length of time the sound is emitted, or both are based at least in part on the determined disturbance score.

8. The method of claim 1, wherein the causing the speaker to emit the sound includes (i) causing the speaker to emit the sound at a first volume and (ii) incrementally increasing the volume from the first volume to a second louder volume over a first period of time.

9. The method of claim 8, wherein the first period of time is 20 seconds.

10. The method of claim 1, wherein the emitted sound is white noise, pink noise, brown noise, or any combination thereof.

11. The method of claim 1, wherein the emitted sound is a soothing sound.

12. The method of claim 11, wherein the soothing sound includes white noise, beach sounds, bird sounds, waterfall sounds, running water sounds, wind sounds, or any combination thereof.

13. The method of claim 1, wherein the respiratory device determines that air is leaking from the mask based at least in part on an analysis of pressure generated by the respiratory device.

14. The method of claim 1, wherein the respiratory device determines that air is leaking from the mask via a leak flow rate estimation algorithm.

15. The method of claim 14, wherein the leak flow rate estimation algorithm receives as inputs a total flow rate, a vent flow rate, a pressure at an interface between the mask and the user, or any combination thereof.

16. The method of claim 1, further comprising:
responsive to the speaker being caused to start emitting the sound, continuing to analyze the first audio data to determine if noise associated with the air leaking is still occurring;
responsive to the continued analysis of the first audio data resulting in a determination that noise associated with the air leaking is still occurring, causing the speaker to continue to emit the sound; and
responsive to the continued analysis of the first audio data resulting in a determination that noise associated with the air leaking from the mask is no longer occurring, (i) determining a length of time that the sound was emitted from the speaker, (ii) responsive to the length of time meeting or exceeding a threshold, causing the speaker to stop emitting the sound, and (iii) responsive to the length of time being below the threshold, causing the speaker to continue emitting the sound until the threshold is met and then causing the speaker to stop emitting the sound.

17. The method of claim 1, further comprising causing the speaker to stop emitting the sound after a predetermined amount of time.

18. A system for masking noises generated during use of a respiratory device, the system comprising:
a respiratory device configured to supply pressurized air;
a mask coupled to the respiratory device, the mask being configured to engage a user during a sleep session to aid in directing the supplied pressurized air to an airway of the user;
a first microphone configured to generate first audio data;
a second microphone configured to generate second audio data;
a speaker configured to emit sound;
a memory storing machine-readable instructions; and a control system including one or more processors configured to execute the machine-readable instructions to:
analyze the first audio data to determine if noise associated with air leaking from the mask is occurring;
responsive to (i) the analysis of the first audio data resulting in a determination that noise associated with air leaking from the mask is occurring, or (ii) the respiratory device determining that air is leaking from the mask, or (iii) both (i) and (ii), further analyze the second audio data to determine if a bed partner of the user is presently disturbed; and
responsive to the further analysis of the second audio data resulting in a determination that the bed partner is presently disturbed, cause the speaker to emit the sound, wherein the emitted sound aids in masking the noise associated with the air leaking from the mask.

19. The system of claim 18, wherein the analysis of the second audio data includes determining if a sleep stage of the bed partner has changed.

20. The system of claim 18, wherein the first microphone is positioned adjacent to a first side of a bed and the respiratory device and the second microphone is positioned adjacent to a second opposing side of the bed and the bed partner.

21. The system of claim 18, further comprising one or more sensors configured to generate motion data, the motion data being indicative of movement by the bed partner of the user.

22. The system of claim 21, wherein the one or more sensors include one or more cameras, one or more video cameras, one or more pressure sensors, one or more accelerometers, one or more gyroscopes, or any combination thereof.

23. The system of claim 21, wherein the second audio data, the motion data, or both are indicative of: movement of the bed partner, rustling of bedding caused by movement of the bed partner, a change in breathing of the bed partner, a change in sleep stage of the bed partner, the bed partner starting to snore, the bed partner speaking, the bed partner sighing, or any combination thereof.

24. The system of claim 18, wherein the analysis of the second audio data includes determining a disturbance score for the bed partner.

25. The system of claim 24, wherein the disturbance score indicates a level of disturbance of the bed partner.

26. The system of claim 24, wherein the disturbance score is a number between 0 and 10, where 0 indicates no disturbance and 10 indicates the highest level of disturbance.

27. The system of claim 24, wherein the sound that is emitted is selected from a plurality of sounds based at least in part on the determined disturbance score.

28. The system of claim 24, wherein a volume of the sound, a length of time the sound is emitted, or both are based at least in part on the determined disturbance score.

* * * * *